United States Patent [19]

Harper et al.

[11] Patent Number: 4,536,516

[45] Date of Patent: Aug. 20, 1985

[54] ALKENE DERIVATIVES

[75] Inventors: Michael J. K. Harper, Ferney-Voltaire, France; Dora N. Richardson; Arthur L. Walpole, deceased, both of Macclesfield, England

[73] Assignee: Imperial Chemical Industries PLC, London, England

[21] Appl. No.: 600,224

[22] Filed: Apr. 17, 1984

Related U.S. Application Data

[63] Continuation of Ser. No. 486,913, Jul. 9, 1974, abandoned, and a continuation of Ser. No. 359,297, Mar. 18, 1982, abandoned, which is a continuation of Ser. No. 918,267, Jun. 22, 1978, abandoned, which is a continuation of Ser. No. 486,774, Jul. 9, 1974, abandoned, which is a continuation-in-part of Ser. No. 262,939, Jun. 15, 1972, abandoned, which is a continuation of Ser. No. 868,667, Oct. 13, 1969, abandoned, which is a continuation of Ser. No. 632,536, Apr. 21, 1967, abandoned, which is a continuation-in-part of Ser. No. 532,891, Mar. 9, 1966, abandoned, and Ser. No. 304,652, Aug. 26, 1973, abandoned, said Ser. No. 486,913, is a continuation-in-part of Ser. No. 262,939.

[30] Foreign Application Priority Data

Sep. 13, 1962 [GB] United Kingdom ............... 34989/62
Jul. 20, 1965 [GB] United Kingdom ............... 30755/65

[51] Int. Cl.$^3$ ................ A61K 31/135; A61K 31/205
[52] U.S. Cl. ................................. 514/514; 514/648; 564/324; 260/501.18
[58] Field of Search ............... 564/324; 424/316, 330; 260/501.18

[56] References Cited

U.S. PATENT DOCUMENTS

| | | | |
|---|---|---|---|
| 3,288,806 | 11/1964 | De Wald | 564/324 X |
| 3,341,537 | 9/1967 | Richardson | 564/324 X |
| 4,198,435 | 4/1980 | Richardson | 564/324 X |

FOREIGN PATENT DOCUMENTS

| | | | |
|---|---|---|---|
| 1013907 | 12/1965 | United Kingdom | 564/324 |
| 1064629 | 4/1967 | United Kingdom | 564/324 |
| 1099093 | 1/1968 | United Kingdom | 564/324 |

Primary Examiner—Robert V. Hines
Attorney, Agent, or Firm—Cushman, Darby & Cushman

[57] ABSTRACT

Triphenylalkene derivatives, in particular 1-(p-β-dimethylaminoethyoxyphenyl)-1,2-diphenylbut-1-ene, which possess utility as anti-oestrogens.

6 Claims, No Drawings

ALKENE DERIVATIVES

This application is a continuation of application Ser. No. 359,297, filed Mar. 18, 1982, which is a continuation of application Ser. No. 918,267, filed June 22, 1978, which is a continuation of application Ser. No. 486,774, filed July 9, 1974, which is a continuation-in-part of application Ser. No. 262,939, filed June 15, 1972, which is a continuation of application Ser. No. 868,667, filed Oct. 13, 1969, which is a continuation of application Ser. No. 632,536, filed Apr. 21, 1967, which is a continuation-in-part of application Ser. No. 532,891, filed Mar. 9, 1966, and application Ser. No. 304,652, filed Aug. 26, 1963, all of said prior applications being abandoned. This application is also a continuation of application Ser. No. 486,913, filed July 9, 1974, which is a continuation-in-part of application Ser. No. 262,939 filed June 15, 1972, which is a continuation of application Ser. No. 868,667, filed Oct. 13, 1969, which is a continuation of application Ser. No. 632,536, filed Apr. 21, 1967, which is a continuation-in-part of application Ser. No. 532,891, filed Mar. 9, 1966, and application Ser. No. 304,652, filed Aug. 26, 1963, all of said prior applications being abandoned.

This invention relates to alkene derivatives which have useful therapeutic properties.

The invention is concerned with alkene derivatives of the formula:

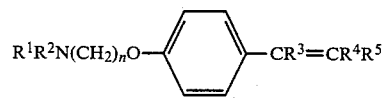

wherein $R^1$ and $R^2$ are both methyl, n is 2, $R^3$ and $R^4$ are both phenyl and $R^5$ is ethyl, and the salts thereof, particularly the pharmaceutically acceptable acid addition salts thereof, and such a compound is named 1-(p-β-dimethylaminoethoxyphenyl)-1,2-diphenylbut-1-ene.

It is clear that a compound of the above formula can exist in the form of two geometric isomers, a cis isomer and a trans isomer, or in the form of a mixture of such isomers. In this specification, the cis isomer is considered to be that isomer in which the phenyls $R^3$ and $R^4$ are in the cis relationship to each with respect to the double bond, and the trans isomer is that in which the phenyls $R^3$ and $R^4$ are in the trans relationship to each other with respect to the double bond. Thus the trans isomer of the above compound has the formula:

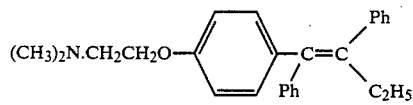

and is named 1-(p-β-dimethylaminoethoxyphenyl)-1,2-trans-diphenylbut-1-ene.

Particular salts of the above alkene derivatives are, for example, a hydrochloride, sulphate, phosphate, acetate, tartrate, oxalate or citrate.

The above alkene derivatives may be prepared by dehydration of the alkanol of the formula:

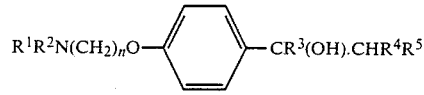

wherein $R^1$, $R^2$, $R^3$, $R^4$, $R^5$ and n are as above.

The dehydration may be carried out by reaction of the alkanol with an acid catalyst, for example hydrochloric acid, conveniently in a solvent, for example ethanol, and by the application of heat.

The alkanol of formula III is obtained by reacting the compound of the formula:

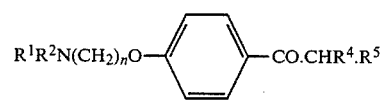

wherein $R^1$, $R^2$, $R^4$, $R^5$ and n are as above, with the Grignard reagent, phenyl magnesium bromide, in an inert solvent. The compound of formula IV is obtained with α-ethyl-4-methoxydesoxybenzoin by demethylation with pyridine hydrochloride at a high temperature to give 4-hydroxy-α-ethyldesoxybenzoin and reaction of the sodium salt of this latter compound with β-dimethylaminoethyl chloride.

The dehydration of the alkanol of formula III produces a mixture of the cis and trans isomers of the alkene of formula I, and this mixture may be separated to give the isolated cis or trans isomer by fractional crystallisation of the alkene of formula I in the form of the free base or a salt, for example a citrate.

As stated above, the alkene derivatives have useful therepeutic properties. These useful properties are in the field of the modification of the reproductive endocrine status in man and animals. In particular, the mixture of isomers obtained by dehydration of the alkanol of formula III shows (a) antifertility effects in rats as demonstrated by its effect in preventing implantation of the fertilised ovum, at a dose of 0.022 mg./kg. on each of days 2, 3 and 4 of pregnancy, and (b) relatively weak oestrogenic activity as demonstrated by the production of cornified vaginal smears in spayed rats at a dose of 9.5 mg/kg. on each of three days; the antifertility effect being due to anti-oestrogenic activity.

These pharmacological properties are qualitatively the same as those of the previously known compound clomiphene which has the structure:

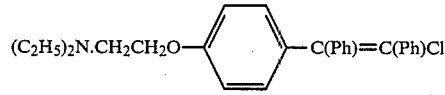

and is also a mixture of geometric isomers. Clomiphene has been previously found to be clinically effective in managing aberrations of the menstrual cycle, in particular in causing the induction of ovulation in women who have failed to ovulate for a variety of reasons, and also in the treatment of hormone dependent tumors, particularly those of the breast. The present mixture of isomers would be expected to be useful in the same clinical conditions as is clomiphene. However, investigation of the isolated cis and trans isomers shows that the cis isomer behaves in all respects as a conventional oestrogen and its antifertility effects in rats are shown only at doses of the same order as those required for oestrogenic effects, whereas the trans isomer shows its antifertility effects in rats by virtue of its antioestrogenic activity and does so at doses well below those required for oestrogenic effect. The trans isomer is substantially more potent in preventing implantation than the cis isomer, and is only very weakly and atypically oestrogenic. Accordingly, the pharmacological properties of the mixture of isomers which are qualitatively the same as those of clomiphene are confined to the trans isomer, and thus the utilisation of these properties in conditions in man where an anti-oestrogenic action would be beneficial, particularly management of aberrations of the menstrual cycle, for example anovulation, or the treatment of hormone dependent tumors without oestrogenic side effects is best carried out by the use of the trans isomer.

Clinical experience with the trans isomer has confirmed that its useful properties are shown at doses in the range 5–100 mg./day. Thus for the treatment of anovulatory infertility, oral doses from 20–80 mg./day administered for 3–5 days have proved effective (Klopper & Hall, Brit.Med.J. 1971, 1, 152; Williamsom & Ellis, J.Obst.Gyn. 1973, 80, 844), and for the treatment of breast tumours, oral doses from 10–40 mg./day have proved effective (Cole, Jones & Todd, Brit.J.Cancer 1971, 25, 270; Ward, Brit.Med.J. 1973, i, 13).

In each of these clinical papers, the authors comment on the low incidence of serious side effects, and this is attributed to the fact that whereas the trans isomer and clomiphene have similar potencies as anti-oestrogens, the trans isomer is very much less oestrogenic than clomiphene and accordingly its use as an anti-oestrogen is accompanied by fewer oestrogenic side effects. The trans isomer is also less effective than clomiphene in causing an undesirable accumulation of desmoesterol.

The mixed isomers and the trans isomers may be used to produce anti-oestrogenic effects in the form of pharmaceutical compositions comprising the active ingredient and a pharmaceutically acceptable diluent or carrier.

Such compositions may be made by conventional methods using conventional excipients, and preferred compositions are those suitable for oral administration, for example tablets. Such tablets may conveniently contain from 1–500 mg. of active ingredient, but usually from 5 to 50 mg.

The compositions may contain in addition to the alkene derivative, another compound known to be useful in modifying the reproductive endocrine system, for example a known progestational agent.

In this specification the desoxybenzoin nucleus is numbered as follows:

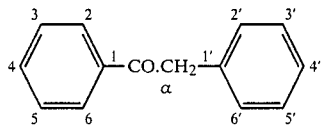

The invention is illustrated but not limited by the following Examples in which the parts are by weight:

EXAMPLE 1

2.15 Parts of 1-(p-β-dimethylaminoethoxyphenyl)-1,2-diphenylbutan-1-ol, 25 parts of ethanol and 0.8 part of 10N-hydrochloric acid are heated together under reflux for 3 hours. The solution is evaporated to dryness under reduced pressure and the residue is extracted with methylene chloride. The methylene chloride extract is decolourised with charcoal and then evaporated to dryness. The residue is dissolved in 100 parts of water, the solution is basified by the addition of sodium hydroxide solution, and the precipitated solid is extracted three times, each time with 50 parts of ether. The combined extracts are dried with anhydrous sodium sulphate and then evaporated. The residue is crystallised from aqueous methanol, and there is thus obtained 1-(p-β-dimethylaminoethoxyphenyl)-1,2-diphenylbut-1-ene, m.p. 95°–96° C. 2 Parts of this compound are stirred together with a solution of 2 parts of citric acid in 10 parts of acetone. The mixture is filtered and the solid residue is crystallised from actone. There is thus obtained 1-(p-β-dimethylaminoethoxyphenyl)-1,2-diphenylbut-1-ene citrate, m.p. 140°–142° C. Treatment of the crude base (i.e., that obtained prior to the crystallisation from aqueous methanol) with citric acid affords a mixture which can be separated by fractional crystallisation into the above citrate of m.p. 140°–142° C. and an isomeric citrate of m.p. 126°–128° C.

The 1-(p-β-dimethylaminoethoxyphenyl)-1,2-diphenylbutan-1-ol used as starting material may be obtained as follows:

To the Grignard reagent prepared from 0.59 part of magnesium, 3.95 parts of bromobenzene and 50 parts of ether there are added 7.5 parts of 4-(β-dimethylaminoethoxy)-α-ethyldesoxybenzoin in 50 parts of ether. After heating under reflux for three hours, the mixture is decomposed by the addition of a solution of 60 parts of ammonium chloride in 150 parts of water. The mixture is separated, and the ethereal layer is dried with anhydrous sodium sulphate, and the ether is evaporated. The residue is crystallised from methanol. There is thus obtained 1-(p-β-dimethylaminoethoxyphenyl)-1,2-diphenylbutan-1-ol, m.p. 120°–121° C.

4-(β-Dimethylaminoethoxy)-α-ethyldesoxybenzoin (b.p. 162° C./0.075 mm.) may be obtained from α-ethyl-4-hydroxydesoxybenzoin by an analogous procedure to that described below for the preparation of 4-(β-dimethylaminoethoxy)-α-methyldesoxybenzoin, and α-ethyl-4-hydroxydesoxybenzoin itself (m.p. 122°–124° C.) may be obtained from α-ethyl-4-methoxydesoxybenzoin by an analogous procedure to that described below for the preparation of 4-hydroxy-α-methyldesoxybenzoin.

The compound, 4-(β-dimethylaminoethoxy)-α-methyldesoxybenzoin, may be obtained as follows:

To a solution of 2.3 parts of sodium in 50 parts of methanol there is added 22.6 parts of 4-hydroxy-α-methyldesoxybenzoin. On evaporation to dryness there is obtained the sodium salt of 4-hydroxy-α-methyldesoxybenzoin. A solution of 21.5 parts of β-dimethylaminoethyl chloride in 150 parts of benzene is added to the above sodium salt, and the mixture is stirred under reflux for 16 hours. The mixture is filtered, and the solvent is removed from the filtrate by evaporation under reduced pressure. The residue is dissolved in 100 parts of 2N-hydrochloric acid, the solution is clarified with charcoal and is then made alkaline by the addition of 10N-sodium hydroxide solution. The mixture is extracted 3 times with 50 parts of ether, the combined extracts are dried (anhydrous sodium sulphate), the solvent is evaporated, and the residue is fractionally distilled in vacuo. There is thus obtained 4-(β-dimethylaminoethoxy)-α-methyldesoxybenzoin, b.p. 178°–180° C./0.5 mm.

4-Hydroxy-α-methyldesoxybenzoin itself may be obtained as follows:

100 Parts of 4-methoxy-α-methyldesoxybenzoin and 250 parts of pyridine hydrochloride are heated together under reflux for 30 minutes. The resulting solution is poured on to 500 parts of ice. The precipitated solid is collected by filtration and dissolved in dilute sodium hydroxide solution. The solution is clarified with charcoal and then acidified with concentrated hydrochloric acid. The mixture is filtered and the solid residue is crystallised from benzene. There is thus obtained 4-hydroxy-α-methyldesoxybenzoin, m.p. 131°–132° C.

EXAMPLE 2

14 Parts of a mixture of the cis and trans isomers of 1-(p-β-dimethylaminoethoxyphenyl)-1,2-diphenylbut-1-ene are crystallised first from petroleum ether (b.p. 40°–60° C.) and then from petroleum ether (b.p. 60°–80° C.). There is thus obtained 1-(p-β-dimethylaminoethoxyphenyl)-1,2-trans-diphenylbut-1-ene, m.p. 96°–98° C. From the mother liquors, the cis isomer 1-(p-β-dimethylaminoethoxyphenyl)-1,2-cis-diphenylbut-1-ene, m.p. 72°–74° C. (after crystallisation from methanol) is obtained.

The mixture of cis and trans isomers used as starting materials may be obtained by conventional means from the mixtures of the salts of the cis and trans isomers, the preparation of which is described in Example 1.

EXAMPLE 3

50 Parts of 1-(p-β-dimethylaminoethoxyphenyl)-1,2-diphenylbut-1-ene citrate of m.p. 140°–142° C., 42 parts of maize starch and 7 parts of alginic acid are intimately mixed and granulated using 10% maize starch paste as the granulating agent. The granules are dried at a temperature not exceeding 50° C., and then mixed with 1 part of magnesium stearate and compressed into tablets each weighing 50 mg. There are thus obtained tablets suitable for oral administration for therapeutic purposes.

What we claim is:

1. The geometric isomer of 1-(p-β-dimethylaminoethoxyphenyl)-1,2-diphenylbut-1ene, and the pharmaceutically acceptable, acid addition salts thereof, which is identified by its citrate having a melting point of 140°–142° C.

2. 1-(p-β-dimethylaminoethoxyphenyl)-trans-1,2-diphenylbut-1-ene and the pharmaceutically acceptable, acid addition salts thereof.

3. 1-(p-β-dimethylaminoethoxyphenyl)-1,2-diphenylbut-1-ene citrate of melting point 140°–142° C.

4. In a process for the treatment of hormone dependent tumors, the improvement which comprises treating said tumors with an effective amount of a member of the group consisting of the geometric isomer of 1-(p-β-dimethylaminoethoxyphenyl)-1,2-diphenylbut-1-ene, and the pharmaceutically acceptable, acid addition salts thereof, which isomer is identified by its citrate having a melting point of 140°–142° C.

5. In a process for the treatment of hormone dependent tumors, the improvement which comprises treating said tumors with an effective amount of a member selected from the group consisting of 1-(p-β-dimethylaminoethoxyphenyl)-trans-1,2-diphenylbut-1-ene and the pharmaceutically acceptable, acid addition salts thereof.

6. In a process for the treatment of hormone dependent tumors, the improvement which comprises treating said tumors with an effective amount of 1-(p-β-dimethylaminoethoxyphenyl)-1,2-diphenylbut-1-ene citrate of melting point 140°–142° C.

* * * * *